(12) United States Patent
Chabansky et al.

(10) Patent No.: US 8,512,348 B2
(45) Date of Patent: Aug. 20, 2013

(54) SURGICAL TOOL FOR ADJUSTING A SPINAL IMPLANT

(75) Inventors: Bruce Chabansky, Palo Alto, CA (US); Bryan A. Click, Fremont, CA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 378 days.

(21) Appl. No.: 13/046,343

(22) Filed: Mar. 11, 2011

(65) Prior Publication Data

US 2012/0232601 A1 Sep. 13, 2012

(51) Int. Cl.
*A61B 17/56* (2006.01)

(52) U.S. Cl.
USPC .......................................... 606/99; 623/17.16

(58) Field of Classification Search
USPC ................. 606/99, 86 A, 914, 90, 915, 900, 606/901, 100, 108, 167, 170, 185, 62–63, 606/232–233; 81/444–449, 451–455, 457; 623/22.12, 17.15, 17.16
See application file for complete search history.

(56) References Cited

U.S. PATENT DOCUMENTS

| | | | |
|---|---|---|---|
| 5,885,299 A * | 3/1999 | Winslow et al. | 606/99 |
| 6,080,175 A * | 6/2000 | Hogendijk | 606/185 |
| 6,174,311 B1 | 1/2001 | Branch et al. | |
| 7,070,598 B2 | 7/2006 | Lim et al. | |
| 7,087,055 B2 | 8/2006 | Lim et al. | |
| 7,655,046 B2 | 2/2010 | Dryer et al. | |
| 7,828,849 B2 | 11/2010 | Lim | |
| 2004/0087947 A1 | 5/2004 | Lim et al. | |
| 2006/0241643 A1 | 10/2006 | Lim et al. | |
| 2008/0140207 A1* | 6/2008 | Olmos et al. | 623/17.16 |
| 2008/0221694 A1* | 9/2008 | Warnick et al. | 623/17.16 |
| 2009/0198241 A1* | 8/2009 | Phan | 606/90 |
| 2010/0057208 A1 | 3/2010 | Dryer et al. | |
| 2011/0054621 A1 | 3/2011 | Lim | |

* cited by examiner

*Primary Examiner* — Todd Manahan
*Assistant Examiner* — Marcela I Shirsat

(57) ABSTRACT

A surgical instrument and/or method of using a surgical instrument during spinal surgery. The surgical instrument may find particular applicability to spinal implants for the intervertebral disc space that require relative rotation between parts in order to change the height of the implant. The instrument includes a knob that rotatable and selectively longitudinally moveable relative to a handle section. In a forward position, turning the knob turns a drive shaft that is coupled to the rotatable actuator of the implant, and causes the implant to expand or retract depending on the direction of rotation. In the rearward position, the drive shaft is retracted, and turning the knob turns a coupling shaft, distinct from the drive shaft, for decoupling the implant from the instrument.

19 Claims, 9 Drawing Sheets

SURGICAL TOOL FOR ADJUSTING A SPINAL IMPLANT

BACKGROUND

The present invention relates generally to medical devices and procedures for orthopedic surgery, particularly to surgical instruments for spinal surgery.

A wide variety of spinal fusion devices are used following partial or total discectomies for stabilization of the spine at that site. Many such devices are secured in the disc space directly between the endplates of the adjacent vertebrae. Some of these devices are changed in height during installation. For example, some of the implants described in U.S. Patent Application Publication No. 2009/0198337 are adapted for implantation in the intervertebral disc space, and are changed in height during implantation. Some examples of suitable instruments for installation of such implants are discussed in U.S. Patent Application Publication No. 2009/0198245. While such implants and tools are suitable for many situations, there remains a need for alternative designs.

SUMMARY

In one embodiment, the present invention is directed to a surgical instrument and/or method of using a surgical instrument during spinal surgery. For example, one or more embodiments of the present invention are directed to a surgical instrument that finds particular applicability to spinal implants for the intervertebral disc space that require relative rotation between parts in order to change the height of the implant. Such an instrument includes a knob that is rotatable and selectively longitudinally moveable relative to a handle section. In a forward position, turning the knob turns a drive shaft that is coupled to the rotatable actuator of the implant, and causes the implant to expand or retract depending on the direction of rotation. In the rearward position, the drive shaft is retracted, and turning the knob turns a coupling shaft, distinct from the drive shaft, for decoupling the implant from the instrument.

In some embodiments, the present invention provides a surgical tool with a handle section, a knob, an inner drive shaft, a coupling shaft, and an outer shaft. The knob is rotatably coupled to the handle section for rotation relative thereto and disposed proximally relative thereto. The inner drive shaft is rotatably supported by the handle section and selectively longitudinally moveable relative thereto. The drive shaft is rotationally fixed relative to the knob for rotation therewith relative to the handle section. The drive shaft has a drive recess at a distal end thereof. The coupling shaft is rotatably supported by the handle and selectively coupled to the knob for rotation therewith relative to the handle section. The coupling shaft is disposed about the drive shaft and has an externally threaded distal end section. The outer shaft is supported by the handle and fixed rotationally longitudinally relative thereto. The outer shaft is disposed about the coupling shaft and has at least one, and preferably two, distally extending alignment flanges on a distal end thereof. The tool has a first configuration wherein: 1) the drive recess, the threaded section, and the alignment flange longitudinally overlap; and 2) the knob is rotationally decoupled from coupling shaft. The tool also has a second configuration wherein: 1) the drive shaft is retracted such that the drive recess is closer to the handle section than in the first operating mode; and 2) the knob is rotationally coupled to the coupling shaft for rotation therewith relative to the handle section.

The drive shaft, the coupling shaft, and the orienting shaft are advantageously disposed along a common longitudinal axis. The knob and drive shaft may be spring biased proximally relative to the handle. The tool may have an indicator associated with the handle and longitudinally moveable thereto by rotation of the knob relative to the housing when the tool is in the first configuration. The rotation of the knob relative the handle does not longitudinally displace the indicator in the second configuration. The tool may have a configuration lock operative to allow the tool to change from the first configuration to the second configuration when moved to a release position relatively farther from a longitudinal axis of the coupling shaft than a lock position. The configuration lock may be biased toward the lock position. With the tool in the second configuration and the configuration lock in the lock position, the drive shaft may be prevented from moving distally such that the drive recess longitudinally overlaps the alignment flange. The coupling shaft may be slidably disposed in the orienting shaft and longer than the orienting shaft such that a proximal end of the coupling shaft longitudinally overlaps the configuration lock. The coupling shaft may be longitudinally moveable relative to the handle section. There may be a resilient bias element disposed in the handle section biasing the knob proximally. The drive recess may be longitudinally non-overlapping with the alignment flange when the tool is in the second configuration. The orienting shaft may have at least two distally extending alignment flanges on a distal end thereof disposed approximately 180° apart circumferentially relative to a longitudinal axis of the orienting shaft. The knob may comprise a knob drive section extending into the handle section, with the knob drive section having a female section that rotationally interlocks with a male section of the coupling shaft when the tool is in the second configuration. The tool may further include a gear rotatably mounted in the handle section, but longitudinally fixed relative thereto, with the gear rotationally coupled to the knob for rotation relative to the handle in the first configuration, but rotationally decoupled from the knob in the second configuration. The orienting shaft may include a tube section extending proximally from the handle section and a proximal end portion, with the proximal end portion having a larger cross section than the tube portion, and the proximal end portion including the alignment flange(s).

In other embodiments, the present invention provides a surgical tool with a handle section, a knob, an inner drive shaft, a coupling shaft, an outer shaft, a configuration lock, and a biasing element (e.g., spring). The knob is rotatably coupled to the handle section for rotation relative thereto and disposed proximally relative thereto. The knob is selectively moveable distally toward the handle section and proximally away from the handle section. The inner drive shaft is rotationally fixed relative to the knob for rotation therewith relative to the handle section. The drive shaft has a non-round drive recess at a distal end thereof. The drive shaft also extends distally relative to the handle section. The coupling shaft is rotatably supported by the handle section and selectively coupled to the knob for rotation therewith relative to the handle section. The coupling shaft is disposed about the drive shaft and has an externally threaded distal section. The outer shaft extends distally from the handle section. The outer shaft is supported by the handle section and fixed relative to the handle section. The outer shaft is disposed about the coupling shaft and the drive shaft. The outer shaft has at least two distally extending alignment flanges on a distal end thereof. The configuration lock is mounted to the housing section and moveable between a locked position and an unlocked position. The configuration lock is selectively engagable with the knob to control movement of the tool between a first configuration and a second configuration. When the tool is in the first configuration: 1) the drive recess, the threaded section, and the alignment flanges longitudinally overlap; and 2) the knob is rotationally decoupled from coupling shaft. When the tool is in the second configuration: 1) the drive shaft is retracted such that the drive recess is closer to the handle section than in the first configuration; 2) the knob is rotationally coupled to the coupling shaft for rotation therewith relative to the handle; and 3) the knob is displaced more proximally relative to the handle section than in the first configuration. The biasing element biases the knob proximally relative to the handle section.

In various embodiments, the present invention has one or more of the above attributes, alone or in any combination.

DETAILED DESCRIPTION

Figure 1:
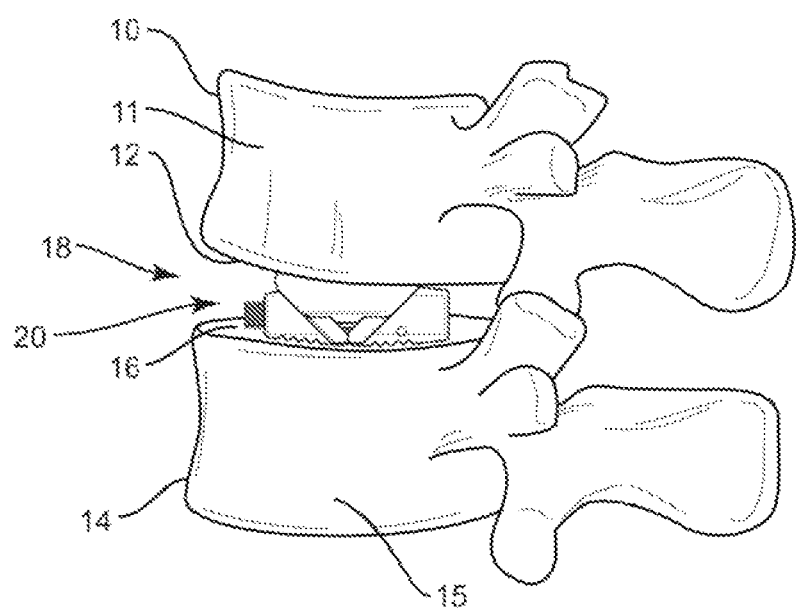
FIG. 1 shows an expanded implant in a disc space.

In one embodiment, the present invention is directed to a surgical instrument and/or method of using a surgical instrument during spinal surgery. For example, one or more embodiments of the present invention are directed to a surgical instrument 40 that finds particular applicability to spinal implants for the intervertebral disc space 18 that require relative rotation between parts in order to change the height of the implant 20. Such an instrument 40 includes a knob 70 that is rotatable and selectively longitudinally moveable relative to a handle section 50. In a forward position, turning the knob 70 turns a drive shaft 100 that is coupled to the rotatable actuator 30 of the implant 20, and causes the implant 20 to expand or retract depending on the direction of rotation. In the rearward position, the drive shaft 100 is retracted, and turning the knob 70 turns a coupling shaft 90, distinct from the drive shaft 100, to decouple the implant 20 from the instrument 40.

In order to provide illustrative context, the following discussion will focus primarily on use of the invention for spinal surgery in the lumbar region of the spine, but it should be understood that the invention may alternatively or additionally be used in other regions of the spine. FIG. 1 depicts adjacent vertebrae 10,14 of the lumbar region of a human spinal column. Each vertebrae 10,14 comprises a corresponding vertebral body 11,15, a superior articular process, a transverse process, an inferior articular process, and a spinous process. In addition, between vertebral bodies 11,15 is a space 18 normally occupied by an intervertebral disc and bounded by the endplates 12, 16 of the vertebral bodies. Due to various conditions, such as a collapsed disc, it may be desired to place an implant in the disc space 18 in order to provide proper structural continuity between the vertebral bodies 11,15. The surgical instrument of the present invention provides a convenient means for delivery of the implant to the desired location and adjustment thereof once positioned.

Figure 2:
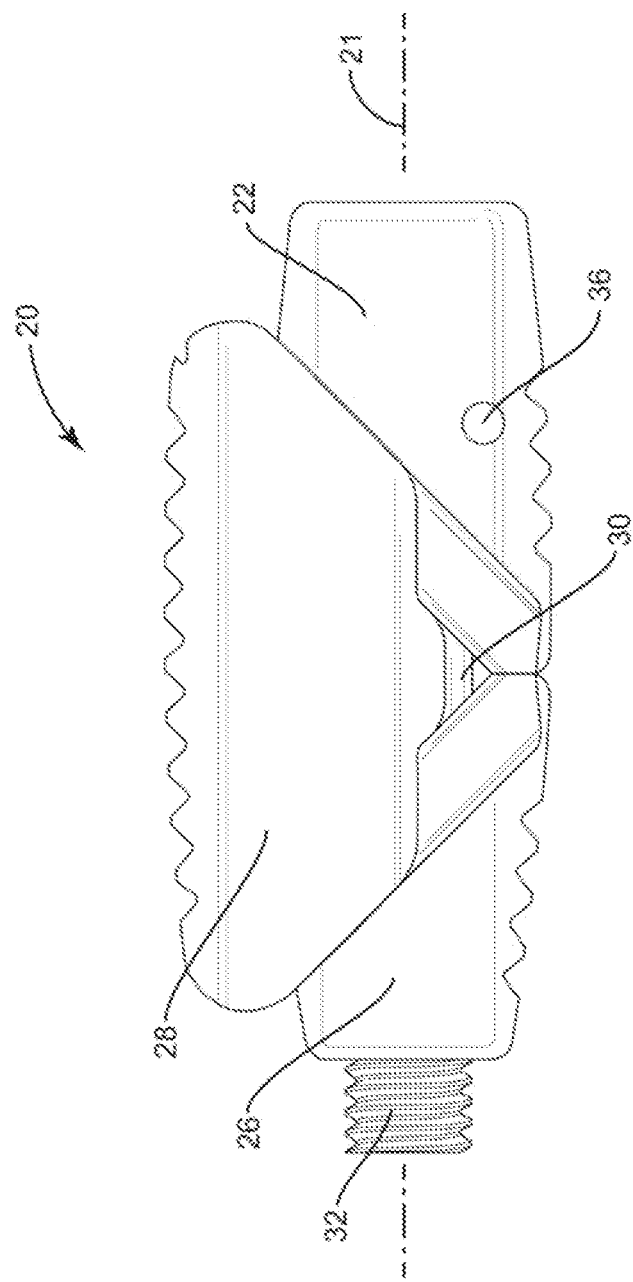
FIG. 2 shows an exemplary implant in an expanded condition.
Figure 3:
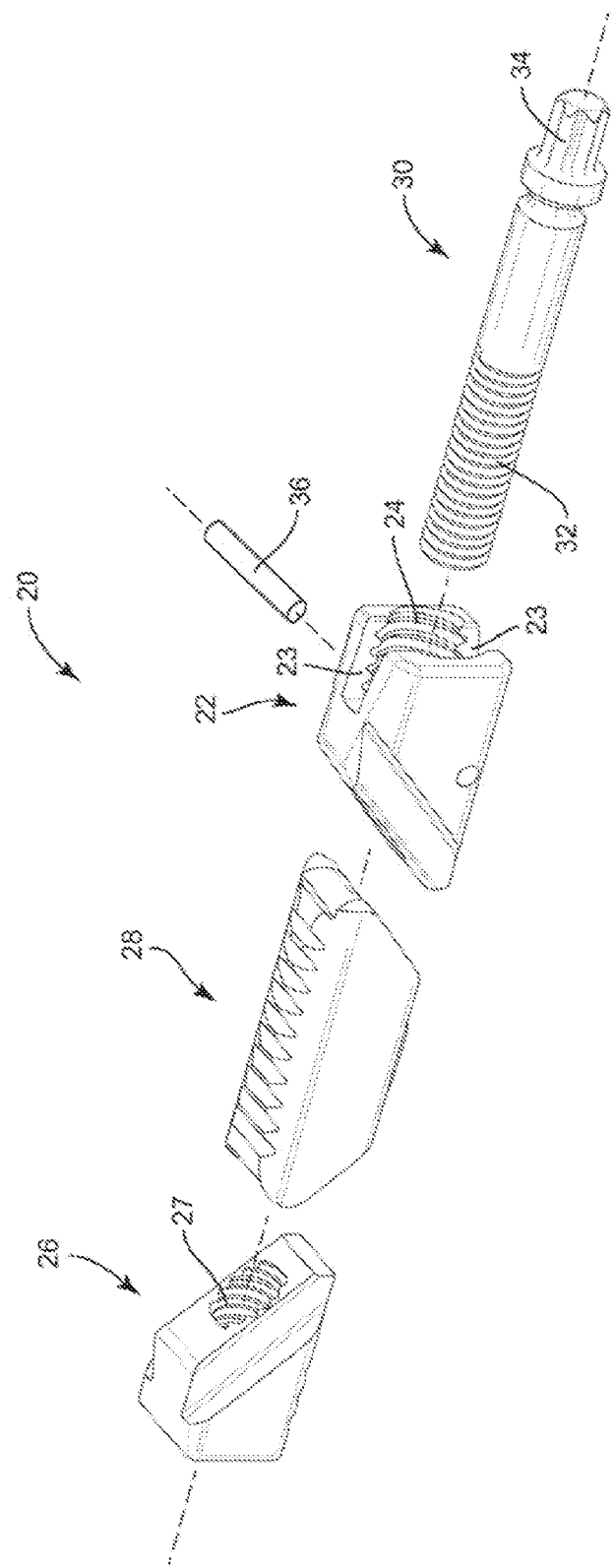
FIG. 3 shows an exploded view of the implant of FIG. 2.
Figure 4:
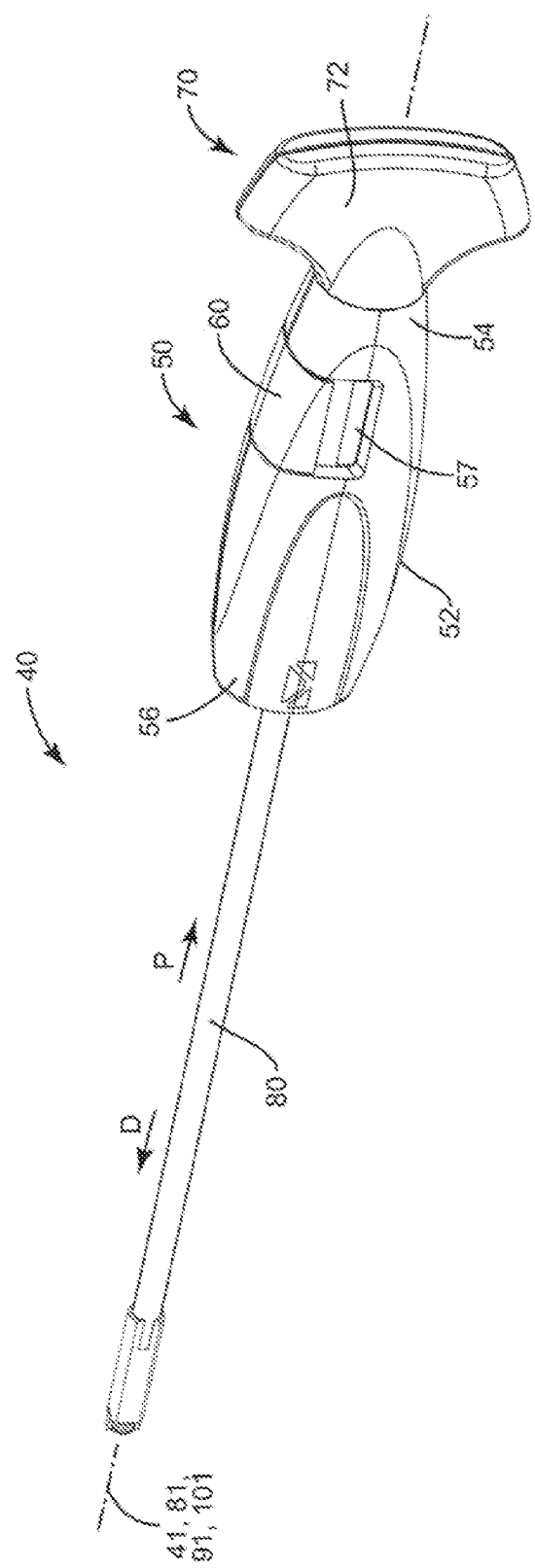
FIG. 4 shows the implant of FIG. 2 attached to an instrument according to one embodiment of the present invention.

The implant 20 may take a variety of forms. In an exemplary embodiment shown in FIGS. 2-3, the implant 20 includes a proximal section 22, a distal section 26, and an intervening middle section 28. The proximal and distal sections 22,26 are movable relative to the middle section 28 to expand the height of the implant 20. An actuation screw 30 extends through the proximal section 22, the middle section 28, and engages the distal section 26. The actuation screw 30 is longitudinally fixed relative to the proximal section 22 via pin 36, but is rotatable relative thereto. The distal end of the actuation screw 30 is threadingly engaged with a threaded bore 27 of the distal section 26. When the actuation screw 30 is tightened, the distal section 26 is pulled toward the proximal section 22, resulting in vertical displacement relative to the middle section 28 due to the wedge shape of the sections 22,26,28. To facilitate rotation of the actuation screw 30, the actuation screw 30 includes an appropriately shaped, e.g., hexalobular, drive end 34 and the proximal section 22 includes partial threads 24 and at least one, and advantageously two, longitudinally running notches 23. For additional information about implants, see U.S. Patent Application Publication Nos. 2009/0198337 and 2009/0198245. Of course, other forms of implants may be employed without departing from the invention. However, the instrument 40 described below is particularly adapted for use with implants that are actuated by rotation of an actuator, such as actuation screw 30, relative to a proximal section of the implant to which the actuator is mated.

One embodiment of the surgical instrument 40 according to the present invention is shown in FIGS. 4-9. The instrument 40 includes a handle section 50, a knob 70, a drive shaft 100, a coupling shaft 90, and an outer or orienting shaft 80. Overall the instrument 40 or tool is elongated along a longitudinal axis 41. For ease of reference, the distal longitudinal direction D (away from the surgeon) may be referred to as the forward direction, and the proximal longitudinal direction P (closer to the surgeon) may be referred to as the rearward direction. The handle section 50 includes a housing 52 having an interior 58. The housing 52 has the knob 70, drive shaft 100, coupling shaft 90, and orienting shaft 80 mounted thereto, and acts as one of the primary gripping portions of the instrument 40. A window 57 in the housing 52 opens to the interior 58 so as to expose an indicator bar 64, as discussed below. A configuration lock 60 is moveably mounted to the upper portion of the housing 52, and is operative to either lock the knob 70 in a forward position, or to allow the knob 70 to move rearward, as discussed further below.

The knob 70 is rotatably mounted to the handle section 50. The knob 70 includes a gripping section 72 and a drive section 74. The gripping section 72 advantageously takes the form of one or two outwardly extending flanges 73 that extend in a plane containing the longitudinal axis 41. The flanges 73 form a convenient means for the surgeon to grip the knob 70 in one hand between the surgeon's thumb and the surgeon's fingers, so as to rotate the knob 70 when desired. The forward portion of the knob 70 forms a drive section 74. The drive section 74 extends into the interior 58 of handle section 50 and is hollow.

The proximal end of the drive section 74 includes a recess 78 with a contoured cross sectional shape, such as hexagonal. This recess 78 is intended to engage either a gear 62 or a proximal section 92 of the coupling shaft 90, depending on the longitudinal position of the knob 70. The drive section 74 also includes two spaced apart collar flanges 75,76. The forward flange 75 is intended to engage the configuration lock 60 when the knob 70 is in the forward position so as to prevent the knob 70 from being moved rearward relative to the handle section 50. The rearward flange 76 is intended to engage the housing 52 to prevent the knob 70 from being disassociated from the handle section 50.

Figure 5:
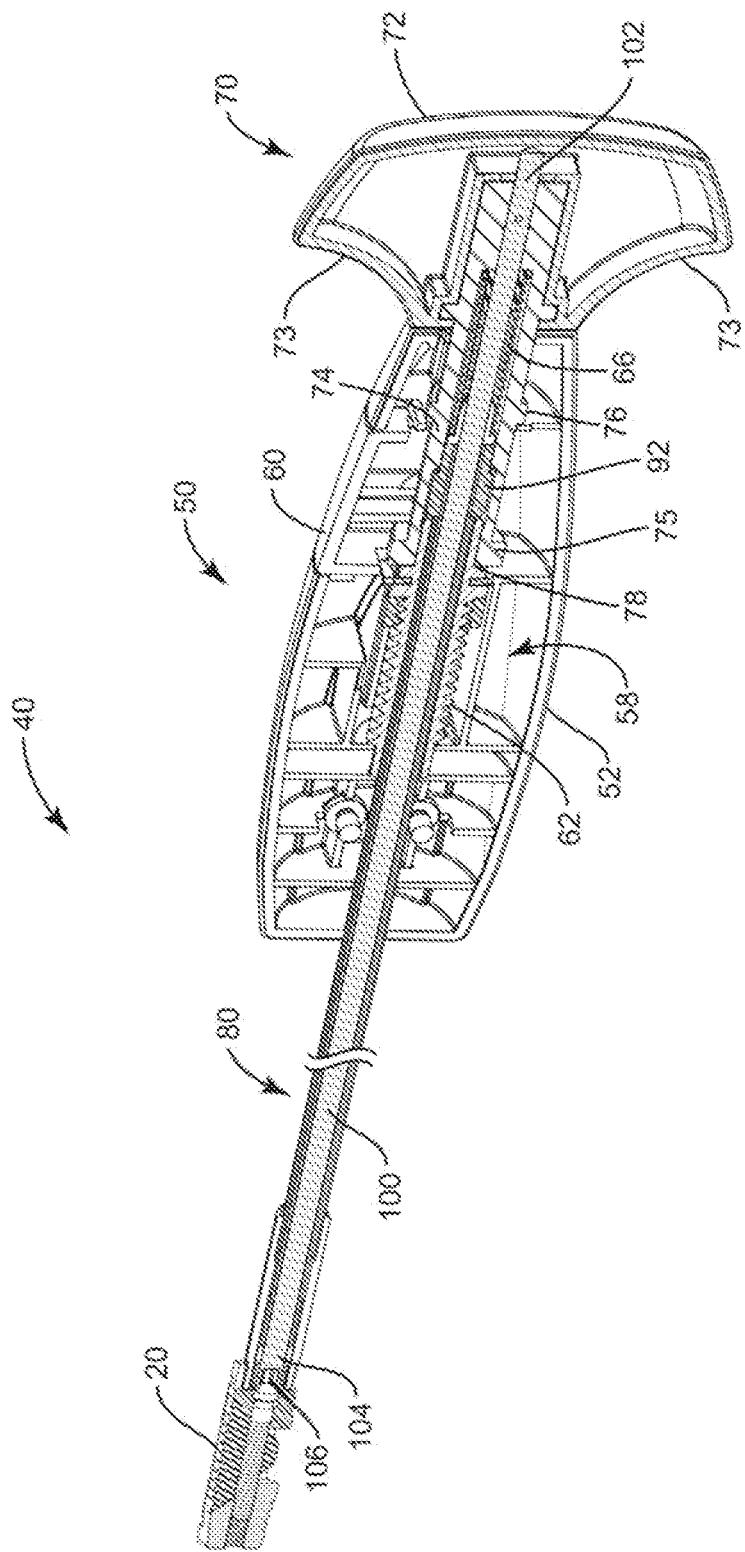
FIG. 5 shows a longitudinal cross section of the instrument of FIG. 4, with the implant attached, in the first or deployed configuration and the configuration lock in the locked position.
Figure 6:
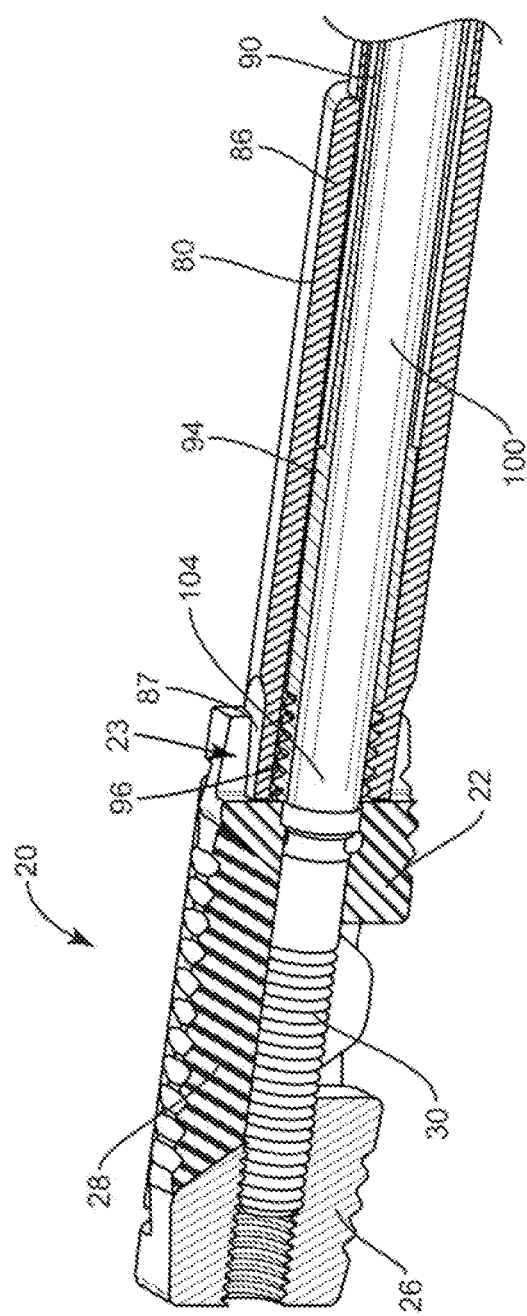
FIG. 6 shows a more detailed view of a portion of FIG. 5.
Figure 7:
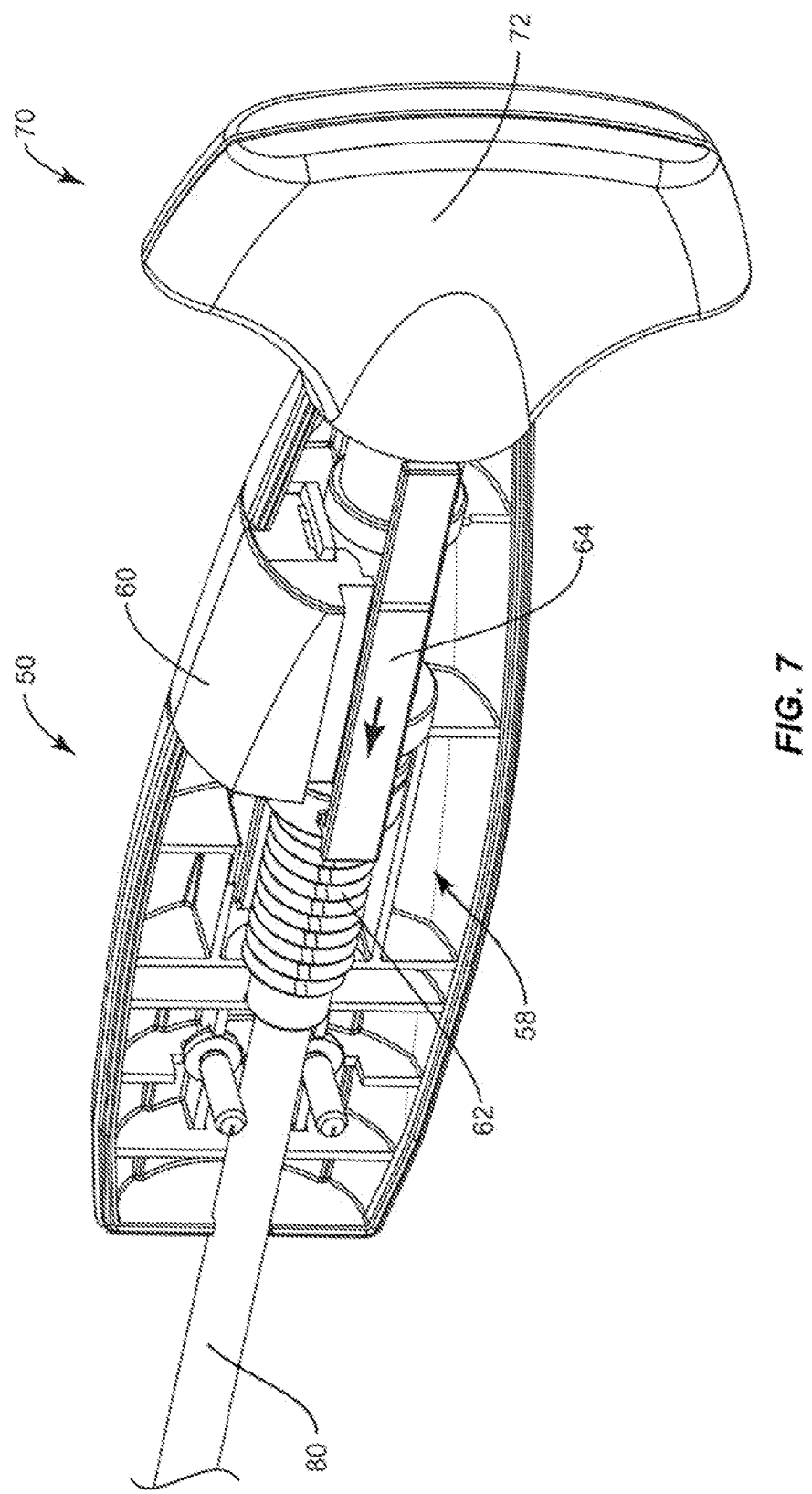
FIG. 7 shows a cross sectional view of the handle portion of the instrument of FIG. 4 in the first or deployed configuration with the indicator bar shown for clarity.
Figure 8:
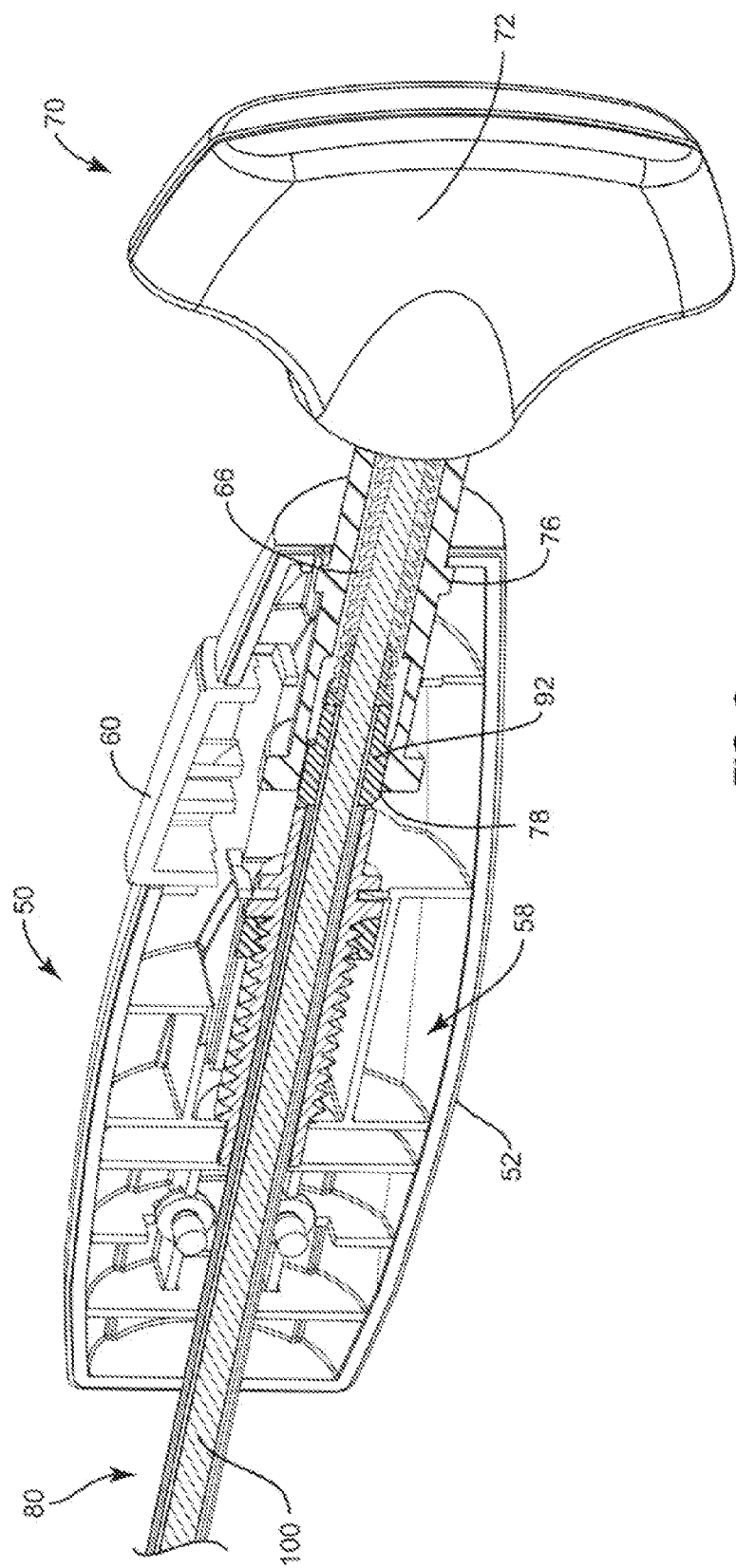
FIG. 8 shows a cross sectional view of the handle portion of the instrument of FIG. 4 in the second or retracted configuration, and with the configuration lock in the unlocked position.
Figure 9:
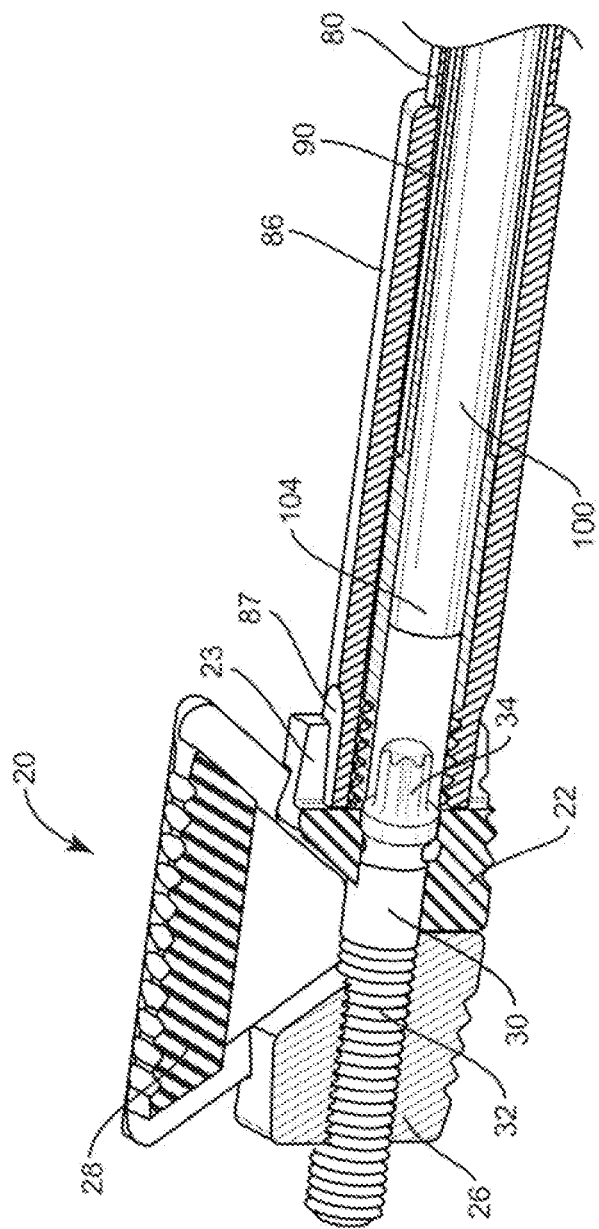
FIG. 9 shows a more detailed view of the implant coupled to the instrument of FIG. 4 when the instrument is in the second or retracted configuration, and the coupling shaft is partially disengaged from the implant.

The orienting shaft 80 is an elongate body that extends along a longitudinal axis 81 from a proximal section 82 to a distal section 86. The orienting shaft 80 is disposed about the coupling shaft 90, and surrounds a substantial length thereof. The proximal section 82 of the orienting shaft 80 is fixedly mounted to the housing 52 of the handle section 50. The proximal section 82 may be mounted to the housing 52 via any suitable method, such as by snap-fitting, adhesives, clamping, etc. For example, a mounting block may be formed on the orienting shaft 80 and used to anchor the proximal section 82 to the housing 52 so as to prevent relative movement, both longitudinal displacement and rotational displacement, between the two. If desired, such a mounting block may have a spring arm extending proximally therefrom that acts to bias the configuration lock 60 to its locked position (closer to the longitudinal axis). The distal section 86 takes the form of a tube which is large enough to accommodate the drive shaft 100 and coupling shaft 90 therein. The distal section 86 includes at least one, and advantageously two or more, alignment flanges 87. These alignment flanges 87 extend forwardly and are advantageously located circumferentially opposite each other so as to be generally 180° apart circumferentially. These alignment flanges 87 may advantageously taper in the distal direction. The flanges 87 may be integrally formed as part of distal section 86, or may be formed by a reinforcement that is fixedly attached to the distal section 86, as shown in FIG. 5.

The coupling shaft 90 is an elongate body that extends along a longitudinal axis 91 from a proximal section 92 to a distal section 94. The coupling shaft 90 is disposed about the drive shaft 100, and surrounds a substantial length thereof. The proximal section 92 of the coupling shaft 90 is disposed in the housing 52 of the handle section 50, near the configuration lock 60. The proximal section 92 has a contoured exterior that corresponds to the shape of the recess 78 of the drive section 74 of knob 70. The proximal section 92 may also include a shoulder or other bearing surface for seating spring 66 which is compressed between the proximal section 92 and knob 70 so as to bias the two away from each other. The distal section 94 of the coupling shaft 90 includes an exteriorly threaded section 96 that is intended to engage with corresponding threads 32 on the implant 20, as discussed further below.

The drive shaft 100 is fixedly mounted to the knob 70 so that the drive shaft 100 moves longitudinally and rotationally with the knob 70. For example, the drive shaft distal section 104 may be fixedly joined to the knob 70 by a cross pin, press fit, overmolding, or other fixed coupling known in the art. The drive shaft 100 extends along a longitudinal axis 101 from a proximal end section 102 (attached to knob 70) to a distal section 104. The endface of distal section 104 includes a drive recess 106 that is disposed along the longitudinal axis 101 and opens in the distal direction D. The drive recess 106 is intended to receivingly engage an actuator 30 of the implant 20, as discussed further below. The drive recess 106 has a non-circular cross section, e.g., hexalobular, so that rotation of the drive shaft 100 can be transmitted to the actuator 30 engaged thereby.

The instrument 40 changes its configuration based on the relative position of the knob 70 and the handle section 50. In a first or deployed configuration, the knob 70 is disposed forwardly so that the attached drive shaft 100 is forwardly disposed. See FIG. 7. In this configuration, the alignment flanges 87 of the orienting shaft 80, the threaded section 96 of the coupling shaft 90, and the drive recess 106 of the drive shaft 100 are longitudinally overlapping. Further, in this deployed configuration, the knob 70 is rotationally coupled to the drive shaft 100 due to the fixed attachment between the two, but rotationally decoupled from the coupling shaft 90 and the orienting shaft 80. That is, in the first configuration, rotation of the knob 70 relative to the housing 52 causes the drive shaft 100 to rotate, but does not cause the coupling shaft 90 or orienting shaft 80 to rotate.

In a second or retracted configuration, the knob 70 is relatively rearwardly positioned so that the attached drive shaft 100 is retracted, and the drive section 74 of the knob 70 is engaged with the proximal section 92 of the coupling shaft 90. See FIG. 8. In this retracted configuration, the drive recess 106 of the drive shaft 100 is disposed closer to the handle section 50, and may advantageously be non-overlapping with the alignment flanges 87 of the orienting shaft 80. It is intended that this retracted configuration results in the drive recess 106 being disengaged from the drive end 34 of the actuation screw 30 of the implant 30. See FIG. 9. Further, in this retracted configuration, the knob 70 is rotationally coupled to the coupling shaft 90, but not rotationally coupled to the orienting shaft 80.

In some embodiments, the instrument 40 may include an indicator bar 64 that is movingly disposed in the handle section 50. See FIG. 7. The indicator bar 64 is intended to move in response to rotation of the knob 70 relative to the handle section 50, so as to provide an indication of the amount of deployment of the implant 20. The indicator bar 64 may include a stripe or other indicia thereon that is viewable through window 57. The indicator bar 64 may be moved via engagement with gear 62, in a conventional gear/travelling nut arrangement. The gear 62 is rotatably mounted to the handle section housing 52, but longitudinally fixed relative thereto. The gear 62 turns when the knob 70 is in the forward position and the knob 70 is turned. More particularly, the recess 78 of drive section 74 engages the gear 62 to rotationally couple the gear 62 to the knob 70 when the instrument 40 is in the deployed configuration.

The configuration lock 60 is moveably mounted to the handle section housing 52. When in its lower position, the configuration lock 60 interacts with the forward flange 75 on drive section 74 to prevent rearward longitudinal displacement the knob 70 relative to housing 52, thereby keeping instrument 40 from changing configurations. Thus, the lower position of configuration lock 60, closer to axis 41, may be thought of as the locked position. See FIG. 5. When the configuration lock 60 is in the upper (unlocked) position, the configuration lock 60 is displaced farther outward from the longitudinal axis 41 enough to allow the knob 70 to be longitudinally moved relative to the housing 52. See FIG. 8. This allows the instrument 40 to change configuration. Advantageously, spring 66 applies a proximal bias to knob 70 such that upon movement of the configuration lock 60 to its upper or unlocked position, the knob 70 automatically moves proximally relative to the handle section 50, so that the instrument 40 automatically assumes the retracted configuration. Of course, manual pressure may overcome this bias, thereby allowing the surgeon to reset the instrument 40 to the deployed configuration. The configuration lock 60 may optionally be biased to its locked position by any suitable means, such as a leaf spring bearing against the configuration lock 60.

The instrument 40 may be used in a surgical procedure. The surgical procedure may begin with providing access to the disc space 18 in any conventional manner. The implant 20 is then delivered to the disc space 18 while mounted to the instrument 40. To mount the implant 20 to the instrument 40, the distal end of instrument 40 is inserted into the proximal end of implant 20 so that the alignment flanges 87 rest in the notches 23. The instrument 40 should be in the retracted configuration while this is done, so that the threaded section 96 of coupling shaft 90 may be retracted rearward against its spring bias forward before it engages the implant 20. The knob 70 is then turned clockwise to turn the coupling shaft 90, and thereby engage the thread section 96 with the threads 24 on the implant 20. The knob 70 is turned until the threaded section 96 "bottoms out," firmly but releasably mating the implant 20 to the instrument 40. The configuration lock 60 is then pulled out, and the knob 70 moved forward to both place the tool 40 in the deployed configuration and mate the actuation screw 30 to the drive recess 106 of drive shaft 100. Preferably, this mating of the implant 20 to the instrument 40 is carried out prior to positioning the implant 20 in the disc space 18, but may be carried out after positioning the implant 20 in the disc space 18 if desired. In order to change the height of the implant 20, the knob 70 is turned while the instrument 40 is in the deployed configuration. As indicated above, turning the knob 70 causes the drive shaft 100 to turn, which causes the actuation screw 30 to turn due to the inter-engagement of the actuation screw 30 and the drive recess 106. Turning the knob 70 clockwise increases the implant's height, while turning the knob 70 counter-clockwise decreases the implant's height, so the desired height of the implant 20 may be achieved even if the implant 20 is over-extended during the height-setting process. Due to the interaction of the knob drive section 74, gear 62, and indicator bar 64, the amount of implant expansion may be tracked by the surgeon by viewing the progress of the indicator stripe in housing window 57. Once the desired height is reached, the instrument 40 may be disconnected from the implant 20. To do this, the configuration lock 60 is pulled out so that the knob gripping section 72 is moved proximally away from the handle section 50 so that there is gap in-between, with the result that the tool 40 is placed in the retracted configuration. This has the effect of moving the drive shaft 100 proximally, which causes the drive recess 106 to move proximally to disengage from the actuator screw 30, while maintaining engagement of the threaded section 96 and the implant threads 24. The knob drive section 74 is displaced proximally so as to disengage from the gear 62 and engage with the proximal section 92 of coupling shaft 90. The knob 70 is then turned counter-clockwise to turn the coupling shaft 90 so as to disengage the threaded section 96 from the implant threads 24. Note that the interaction of alignment flanges 87 and notches 23 prevent the implant 20 from rotating relative to the orienting shaft 80 and therefore the handle section 50, during the rotation of coupling shaft 90. meaning that the orientation of the implant 20 in the disc space 18 is not changed when unthreading the threaded section 96 from the implant 20. When fully unthreaded, the instrument 40 is pulled back to remove the alignment flanges 87 from the notches 23, thereby fully decoupling the instrument 40 from the implant 20. The surgical procedure then proceeds in a conventional fashion to clean and close the surgical site. Such a process may be used to install a single implant 20 in the disc space 18, or multiple implants 20 may be installed in the disc space 18, using the same or multiple instruments 40.

The discussions above have been in the context of using the tool 40 with a spinal implant 20 having three relatively moveable sections 22,26,28 that move due to rotation of an actuator 30. However, it should be understood that the instrument 40 may be used with other spinal implants that have less or more sections, whether such are wedge shaped or not. Further, it has been assumed that the configuration lock 60 is pulled out to allow the change in configuration of the tool 40, but such is not required in all embodiments. For example, the configuration lock 40 could be designed to extend "below" the longitudinal axis 41 and engage the drive section 74 from "underneath." Also, the interplay between the configuration lock 60 in the locked position and the knob 70 may allow for some limited longitudinal movement in some embodiments, but still not allow for the tool 40 to change configurations.

For ease of description, it has been assumed that the actuation screw 30 and drive recess 106 have hexalobular cross sections, and that proximal section 92 of coupling shaft 90 and drive section 74 of knob 70 have hexagonal cross sections. However, any suitable cross sectional profile may be used for either, such as star, square, double hexagonal, and the like, whether faceted or not (e.g., oval). Further, the drive section 74 of knob 70 may alternatively engage with gear 62 and proximal section 92 of coupling shaft via other connections, such as spline type connections, indirect gear connections, and the like.

The components of the tool 40 and implant 20 may be made from any suitable materials known in the art. For example, the implant 20 may be formed from biologically compatible stainless steel, titanium and its alloys, polymers such as PEEK, etc. Likewise, the tool 40 may be formed with a stainless steel orienting shaft 80, coupling shaft 90, and drive shaft 100, with a polymer (e.g., ABS, polycarbonate, etc.) housing 52, knob 70, worm gear 62, and configuration lock 60.

All U.S. patents and patent application publications mentioned above are hereby incorporated herein by reference in their entirety.

The present invention may, of course, be carried out in other specific ways than those herein set forth without departing from the scope of the invention. The present embodiments are, therefore, to be considered in all respects as illustrative and not restrictive, and all changes coming within the meaning and equivalency range of the appended claims are intended to be embraced therein.

What is claimed is:

1. A surgical tool, comprising:
   a handle section;
   a knob rotatably coupled to the handle section for rotation relative thereto and disposed proximally relative thereto;
   a inner drive shaft rotatably supported by the handle section and selectively longitudinally moveable relative thereto; the drive shaft rotationally fixed relative to the knob for rotation therewith relative to the handle section; the drive shaft having a drive recess at a distal end thereof;
   a coupling shaft rotatably supported by the handle section and selectively coupled to the knob for rotation therewith relative to the handle section; the coupling shaft disposed about the drive shaft and having an externally threaded distal section;
   an outer shaft extending distally from the handle section; the outer shaft supported by the handle section and fixed rotationally and longitudinally relative to the handle section; the outer shaft disposed about the coupling shaft; the outer shaft having at least one distally extending alignment flange on a distal end thereof;

the tool having a first configuration wherein:
the drive recess, the threaded section, and the alignment flange longitudinally overlap;
the knob is rotationally decoupled from coupling shaft;

the tool having a second configuration wherein:
the drive shaft is retracted such that the drive recess is closer to the handle section than in the first configuration;
the knob is rotationally coupled to the coupling shaft for rotation therewith relative to the handle.

2. The surgical tool of claim 1 wherein the drive shaft, the coupling shaft, and the outer shaft are disposed along a common longitudinal axis.

3. The surgical tool of claim 1 wherein the knob and drive shaft are spring biased proximally relative to the handle section.

4. The surgical tool of claim 1 further comprising an indicator associated with the handle section and longitudinally moveable thereto by rotation of the knob relative to the handle section when the tool is in the first configuration; wherein rotation of the knob relative the handle section does not longitudinally displace the indicator in the second configuration.

5. The surgical tool of claim 1 further comprising a configuration lock; the configuration lock operative to inhibit the tool from changing from the first configuration to the second configuration when in a lock position relatively closer to a longitudinal axis of the coupling shaft than a release position; wherein the configuration lock, in the release position, allows the tool to change from the first configuration to the second configuration.

6. The surgical tool of claim 5 wherein the configuration lock is biased toward the lock position.

7. The surgical tool of claim 5 wherein the coupling shaft is slidably disposed in the outer shaft and longer than the outer shaft such that a proximal end of the coupling shaft longitudinally overlaps the configuration lock.

8. The surgical tool of claim 5 wherein, with the tool in the second configuration and the configuration lock in the lock position, the drive shaft is prevented from moving distally to the point that the drive recess longitudinally overlaps the alignment flange.

9. The surgical tool of claim 1 wherein the coupling shaft is longitudinally moveable relative to the handle section.

10. The surgical tool of claim 1 wherein the tool further comprises a resilient bias element disposed in the handle section biasing the knob proximally.

11. The surgical tool of claim 1 wherein the drive recess is longitudinally non-overlapping with the alignment flange when the tool is in the second configuration.

12. The surgical tool of claim 1 wherein the outer shaft has at least two distally extending alignment flanges on a distal end thereof disposed approximately 180° apart circumferentially relative to a longitudinal axis of the outer shaft.

13. The surgical tool of claim 1 wherein the knob comprises a knob drive section extending into the handle section; wherein the knob drive section comprises a female section that rotationally interlocks with a male section of the coupling shaft when the tool is in the second configuration.

14. The surgical tool of claim 1 further comprising a gear rotatably mounted in the handle section, but longitudinally fixed relative thereto; wherein the gear is rotationally coupled to the knob for rotation relative to the handle in the first configuration; wherein the gear is rotationally decoupled from the knob in the second configuration.

15. The surgical tool of claim 1 wherein the outer shaft comprises a tube section extending proximally from the handle section and a proximal end portion; wherein the proximal end portion has a larger cross section than the tube portion; wherein the proximal end portion comprises the alignment flange.

16. The surgical tool of claim 1 wherein the drive recess is configured to receivingly engage a hexalobular fastener.

17. A surgical tool, comprising:
a handle section;
a knob rotatably coupled to the handle section for rotation relative thereto and disposed proximally relative thereto; the knob selectively moveable distally toward the handle section and proximally away from the handle section;
an inner drive shaft rotationally fixed relative to the knob for rotation therewith relative to the handle section; the drive shaft having a non-round drive recess at a distal end thereof; the drive shaft extending distally relative to the handle section;
a coupling shaft rotatably supported by the handle section and selectively coupled to the knob for rotation therewith relative to the handle section; the coupling shaft disposed about the drive shaft and having an externally threaded distal section;
an outer shaft extending distally from the handle section; the outer shaft supported by the handle section and fixed relative to the handle section; the outer shaft disposed about the coupling shaft and the drive shaft; the outer shaft having at least two distally extending alignment flanges on a distal end thereof;
a configuration lock mounted to the housing section and moveable between a locked position and an unlocked position; the configuration lock selectively engagable with the knob to control movement of the tool between a first configuration and a second configuration;
wherein when the tool is in the first configuration:
the drive recess, the threaded section, and the alignment flanges longitudinally overlap;
the knob is rotationally decoupled from coupling shaft;
wherein when the tool is in the second configuration:
the drive shaft is retracted such that the drive recess is closer to the handle section than in the first configuration;
the knob is rotationally coupled to the coupling shaft for rotation therewith relative to the handle;
the knob is displaced more proximally relative to the handle section than in the first configuration;
a biasing element biasing the knob proximally relative to the handle section.

18. The surgical tool of claim 17 wherein the coupling shaft extends more proximally than the outer shaft and wherein a proximal end of the coupling shaft longitudinally overlaps the configuration lock.

19. The surgical tool of claim 17 further comprising a indicator flag associated with the handle section and moveably supported thereby such that;
in the first configuration, the knob is coupled to the indicator flag such that rotation of the knob relative to the handle section causes longitudinal displacement of the indicator flag relative to the handle section;
in the second configuration, rotation of the knob relative the handle section does not longitudinally displace the indicator flag relative to the handle section.

* * * * *